(12) United States Patent
Craun et al.

(10) Patent No.: US 9,493,674 B2
(45) Date of Patent: *Nov. 15, 2016

(54) SYNERGISTIC CATALYST COMBINATION FOR THE PREPARATION OF RADIATION CURABLE OLIGOMERS

(71) Applicant: Akzo Nobel Coatings International B.V., Arnhem (NL)

(72) Inventors: Gary Pierce Craun, Berea, OH (US); Gary Charles Pompignano, Wadsworth, OH (US)

(73) Assignee: AKZO NOBEL COATINGS INTERNATIONAL B.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/837,946

(22) Filed: Aug. 27, 2015

(65) Prior Publication Data

US 2015/0368475 A1    Dec. 24, 2015

Related U.S. Application Data

(63) Continuation of application No. 14/769,566, filed as application No. PCT/EP2014/054518 on Mar. 10, 2014.

(60) Provisional application No. 61/777,415, filed on Mar. 12, 2013.

(30) Foreign Application Priority Data

May 23, 2013  (EP) .................................... 13168831

(51) Int. Cl.
| | |
|---|---|
| *C08L 63/00* | (2006.01) |
| *C09D 171/00* | (2006.01) |
| *C08K 5/521* | (2006.01) |
| *C09D 133/06* | (2006.01) |
| *C09D 133/14* | (2006.01) |
| *C09D 143/02* | (2006.01) |
| *C09D 193/00* | (2006.01) |
| *C07C 67/29* | (2006.01) |
| *C09D 4/00* | (2006.01) |
| *B05D 3/06* | (2006.01) |
| *C08F 220/18* | (2006.01) |

(52) U.S. Cl.
CPC ............. *C09D 171/00* (2013.01); *B05D 3/067* (2013.01); *B05D 3/068* (2013.01); *C07C 67/29* (2013.01); *C08K 5/521* (2013.01); *C08L 63/00* (2013.01); *C09D 4/00* (2013.01); *C09D 133/066* (2013.01); *C09D 133/14* (2013.01); *C09D 143/02* (2013.01); *C09D 193/00* (2013.01); *C08F 220/18* (2013.01); *C08L 2312/06* (2013.01)

(58) Field of Classification Search
CPC .... B05D 3/067; C09D 133/12; C08K 5/521; C08K 5/49; C08L 63/00; C08L 2312/06; C08F 220/18
See application file for complete search history.

(56) References Cited

U.S. PATENT DOCUMENTS

| | | | |
|---|---|---|---|
| 4,434,278 A | 2/1984 | Skiscim | |
| 4,503,173 A | 3/1985 | Martino et al. | |
| 4,992,525 A | 2/1991 | Kriessmann et al. | |
| 5,708,093 A | 1/1998 | Bastelberger et al. | |
| 2004/0134791 A1 | 7/2004 | Toi et al. | |
| 2008/0302694 A1* | 12/2008 | Gardner | C08G 18/6725 206/524.3 |
| 2010/0167072 A1 | 7/2010 | Chouai et al. | |

FOREIGN PATENT DOCUMENTS

| | | |
|---|---|---|
| EP | 0541169 A1 | 5/1993 |
| GB | 2428678 B | 2/2007 |
| JP | S55-139464 A | 10/1980 |
| JP | H03-192174 A | 8/1991 |
| JP | H05-179177 A | 7/1993 |
| JP | H08-325509 A | 12/1996 |
| JP | 2005-089712 A | 4/2005 |
| JP | 2005-320453 A | 11/2005 |
| JP | 2006-152056 A | 6/2006 |
| WO | 93/20122 A1 | 10/1993 |
| WO | 2008/151286 A1 | 12/2008 |
| WO | 2010100121 A1 | 9/2010 |
| WO | 2012089746 A1 | 7/2012 |

OTHER PUBLICATIONS

Guo et al "Hydrolysis of Epoxidized Soybean Oil in the Presence of Phosphoric Acid", Journal of the American Oil Chemists' Society, Oct. 2007, vol. 84, Issue 10, pp. 929-935.*
Zhong et al, "Novel Coatings From Soybean Oil Phosphate Ester Polyols," Journal of Coatings Technology,' vol. 73, No. 915, Apr. 2001, pp. 53-57.

(Continued)

*Primary Examiner* — Gregory Listvoyb
(74) *Attorney, Agent, or Firm* — Alice C. Su

(57) ABSTRACT

Radiation curable coating compositions are disclosed. In some embodiments, the coating compositions are used to coat substrates such as packaging materials and the like for the storage of food and beverages. The coating compositions may have a (meth)acrylate functional polyether polyol prepared by reacting an epoxidized vegetable oil in the presence of a phosphoric acid compound to form an epoxy phosphate, and reacting the epoxy phosphate with a hydroxyl functional (meth)acrylate in the presence of an acid catalyst to form the (meth)acrylate functional polyether polyol.

18 Claims, No Drawings

(56) References Cited

OTHER PUBLICATIONS

Mannari, et al, Two-Component High-Solid Polyurethane Coating Systems Based on Soy Polyols,' JCT Research, vol. 3, No. 2, Apr. 2006, pp. 151-157.
Mannari, et al, "Epoxy Acid Phosphate Esters-Dispersibility and Salt Fog Resistance," Proceedings of the Thirtieth International Waterborne, High-Solids, and Powder Coatings Symposium,' Presented at the International Waterborne, High-Solids, and Powder Coatings Symposium, Feb. 26-28, 2003, New Orleans, LA, pp. 415-421.
Search Report and Written Opinion of International Application No. PCT/EP2014/054518, mailed May 6, 2014.
Search Report of EP Application No. 13168831.9, dated Oct. 16, 2013.
Guo et al, "Hydrolysis of Epoxidized Soybean Oil in the Presence of Phosphoric Acid," Springer AOCS, Sep. 21, 2005.

* cited by examiner

SYNERGISTIC CATALYST COMBINATION FOR THE PREPARATION OF RADIATION CURABLE OLIGOMERS

CROSS-REFERENCE TO RELATED APPLICATIONS

This application is a continuation of U.S. patent application Ser. No. 14/769,566, filed Aug. 21, 2015, which is a national stage filing under 35 U.S.C. §371 of PCT/EP2014/054518, filed Mar. 10, 2014, which claims priority to U.S. Provisional Patent Application No. 61/777,415, filed Mar. 12, 2013, and European Patent Application No. 13168831.9, filed May 23, 2013, the contents of which herein incorporated by reference to the extent not inconsistent with the present disclosure.

BACKGROUND OF THE INVENTION

1. Field of the Invention

The present invention relates to radiation curable coating compositions, methods of coating substrates with the coating compositions, and substrates coated with the coating compositions.

2. Description of Related Art

Many currently available radiation curable coatings, such as those cured with ultra-violet ("UV") radiation or electron beam ("EB") radiation, have a tendency to be inflexible after curing and prone to high levels of shrinkage. Consequently, many radiation curable coatings are recognized to be inadequate in terms of direct to metal adhesion, formability and retort resistance, which are some of the desired properties for rigid packaging coating applications. Adhesion and extensibility inadequacies have been found when the coatings were used for flexible packaging.

Commonly-owned International Patent publication WO 2008/151286 describes radiation curable oligomers prepared from an epoxidized vegetable oil and a hydroxyl functional material in the presence of a strong acid catalyst.

The radiation curable coating compositions of the invention aim to solve some of the aforementioned inadequacies. The coating compositions can be used, inter alia, as packaging coatings for food and beverage packaging and containers. They can be formulated to provide improved adhesion, flexibility, and formability compared to some commercial radiation curable coating compositions.

SUMMARY OF THE INVENTION

Aliphatic epoxide groups in the epoxidized vegetable oils of WO 2008/151286 are generally less reactive than glycidyl epoxy groups. WO 2008/151286 explains that strong acid catalysts such as zinc triflates are suitable to catalyze the reaction of epoxidized vegetable oils with hydroxyl functional compounds. However, even with these strong acid catalysts, hydroxyl functional (meth)acrylates like butane diol monoacrylate and hydroxy ethyl acrylate might thermally polymerize at high temperature, even in the presence of polymerization inhibitors. As a result, it is difficult to prepare radiation curable coating compositions with high conversion from epoxidized vegetable oils and hydroxyl functional (meth)acrylates.

The present invention includes radiation curable coating compositions having a (meth)acrylate functional polyether polyol, processes for producing the coating compositions, methods of coating substrates with the coating compositions, and substrates coated with the coating compositions. Such processes can be performed in a single reactor or in multiple reactors.

In some embodiments of the invention, a coating composition having a (meth)acrylate functional polyether polyol is prepared by a method comprising reacting an epoxidized vegetable oil with a phosphoric acid compound to form an epoxy phosphate, and then reacting the epoxy phosphate with a hydroxyl functional (meth)acrylate in the presence of an acid catalyst to form the (meth)acrylate functional polyether polyol. In some embodiments, the acid catalyst comprises a triflic acid, a triflate salt of a metal of Group IIA, IIB, IIIA, IIIB or VIIIA of the Periodic Table of Elements (according to the IUPAC 1970 convention), a mixture of the triflates salts, or a mixture thereof.

It has been found that a phosphoric acid compound and an acid catalyst function as a synergistic catalyst combination during the preparation of radiation curable coating compositions. The phosphoric acid compound increases the reaction rate of the hydroxyl functional (meth)acrylate with the epoxidized vegetable oil. The phosphate functionality of the epoxy phosphate helps adhere the radiation cured coating composition to the substrate. In addition, the epoxy phosphate significantly enhances the effectiveness of the acid catalyst used to form the (meth)acrylate functional polyether polyol, allowing the acid catalyst to be used at a lower concentration while achieving a higher reaction rate and more complete conversion. As a result, compared to WO 2008/151286, the amount of the acid catalyst can be reduced by a factor of at least about 10, while conversion of the epoxide groups in the epoxidized vegetable oil can be increased from about 90% to about 99.9% at the same reaction temperature and the same reaction time.

The present invention includes methods of coating a substrate by applying the coating composition to the substrate. Substrates coated with the coating compositions are also disclosed. In some embodiments, the substrate is a can or packaging.

DETAILED DESCRIPTION OF THE INVENTION

As used in the afore-discussed embodiments and other embodiments of the disclosure and claims described herein, the following terms generally have the meaning as indicated, but these meanings are not meant to limit the scope of the invention if the benefit of the invention is achieved by inferring a broader meaning to the following terms.

The present invention includes substrates coated at least in part with a coating composition of the invention and methods for coating the substrates. The term "substrate" as used herein includes, without limitation, cans, metal cans, easy-open-ends, packaging, containers, receptacles, or any portions thereof used to hold, touch or contact any type of food or beverage. Also, the terms "substrate", "food can(s)", "food containers" and the like include, for non-limiting example, "can ends", which can be stamped from can end stock and used in the packaging of food and beverages.

The present invention includes coating compositions having a (meth)acrylate functional polyether polyol and methods for preparing the coating compositions. The coating compositions may be prepared by reacting an epoxidized vegetable oil with a phosphoric acid compound to form an epoxy phosphate, and reacting the epoxy phosphate with a hydroxyl functional (meth)acrylate in the presence of an acid catalyst to form the (meth)acrylate functional polyether polyol.

In some embodiments, the phosphoric acid compound includes phosphoric acid, super phosphoric acid, an aqueous solution of the foregoing, or a mixture thereof. In some embodiments, the phosphoric acid compound is present in an amount from about 0.001 to about 25 wt % of the (meth)acrylate functional polyether polyol.

During the reaction of the epoxidized vegetable oil with the phosphoric acid compound, some of the epoxide groups do not react with the phosphoric acid compound. As a result, these epoxide groups are available to react with the hydroxyl functional (meth)acrylate to produce the (meth)acrylate functional polyether polyol.

The epoxidized vegetable oil can be used alone or in combination with other epoxidized vegetable oils. Epoxidized vegetable oils can be prepared from vegetable oils by, for non-limiting example, adding hydrogen peroxide and formic or acetic acid to the vegetable oil, and then holding the mixture at an elevated temperature until some or all of the carbon-carbon double bonds are converted to epoxide groups.

Vegetable oils contain primarily glycerides which are triesters of glycerol and fatty acids with varying degrees of unsaturation. For non-limiting example, epoxidized vegetable oils for use in the invention can be made from vegetable oils (fatty acid triglycerides) such as without limitation, esters of glycerol and fatty acids having an alkyl chain of about 12 to about 24 carbon atoms. Fatty acid glycerides which are triglycerides in unsaturated glyceride oils are generally referred to as drying oils or semidrying oils. Drying oils include, for non-limiting example, linseed oil, perilla oil and combinations thereof, while semidrying oils include, without limitation, tall oil, soy bean oil, safflower oil and combinations thereof. Triglyceride oils in some embodiments have identical fatty acid chains or alternatively have different fatty acid chains attached to the same glycerol molecule. In some embodiments, the oils have fatty acid chains containing non-conjugated double bonds. In some embodiments, single double bond or conjugated double bond fatty acid chains are used in minor amounts. Double bond unsaturation in glycerides can be measured by iodine value (number) which indicates the degree of double bond unsaturation in the fatty acid chains. Unsaturated fatty acid glyceride oils employed in some embodiments of the invention have an iodine value greater than about 25 and alternatively between about 100 and about 210.

Naturally occurring vegetable oils for use in the invention can be for non-limiting example, mixtures of fatty acid chains present as glycerides, and include without limitation a distribution of fatty acid esters of glyceride, where the fatty acid distribution may be random but within an established range that may vary moderately depending on the growing conditions of the vegetable source. Soybean oil is employed in some embodiments which comprises approximately about 11% palmitic, about 4% stearic, about 25% oleic, about 51% linolenic, and about 9% linoleic fatty acids, where oleic, linoleic and linolenic are unsaturated fatty acids. Unsaturated vegetable oils employed in some embodiments of the invention, include without limitation, glyceride oils containing non-conjugated unsaturated fatty acid glyceride esters such as, without limitation, linoleic and linolenic fatty acids.

Unsaturated glyceride oils include, without limitation, corn oil, cottonseed oil, rapeseed oil, hempseed oil, linseed oil, wild mustard oil, peanut oil, perilla oil, poppyseed oil, rapeseed oil, safflower oil, sesame oil, soy bean oil, sunflower oil, canola oil, tall oil, and mixtures thereof. Fatty acid glycerides for use in the invention include, for non-limiting example, those which contain linoleic and linolenic fatty acid chains, oils such as without limitation, hempseed oil, linseed oil, perilla oil, poppyseed oil, safflower oil, soy bean oil, sunflower oil, canola oil, tall oil, grapeseed oil, rattonseed oil, corn oil, and similar oils which contain high levels of linoleic and linolenic fatty acid glyceride. Glycerides can contain lesser amounts of saturated fatty acids in some embodiments. For non-limiting example, soy bean oil can be employed which contains predominantly linoleic and linolenic fatty acid glycerides. Combinations of such oils are employed in some embodiments of the invention. Vegetable oils can by fully or partially epoxidized by known processes, such as for non-limiting example, using acids such as, without limitation, peroxy acid for epoxidation of unsaturated double bonds of the unsaturated vegetable oil. Unsaturated glyceride oils employed in some embodiments include mono-, di-glycerides and mixtures thereof with tri-glycerides or fatty acid esters of saturated and unsaturated fatty acids.

In some embodiments, the epoxidized vegetable oil comprises corn oil, cottonseed oil, grapeseed oil, hempseed oil, linseed oil, wild mustard oil, peanut oil, perilla oil, poppyseed oil, rapeseed oil, safflower oil, sesame oil, soy bean oil, sunflower oil, canola oil, tall oil, a fatty acid ester, monoglyceride or diglyceride of such oils, or a mixture thereof.

Commercially available sources of epoxidized vegetable oils are used in some embodiments of the invention such as, for non-limiting example, epoxidized soy oil sold under the trade designations "VIKOLOX" and "VIKOFLEX 7170" available from Arkema, Inc, "DRAPEX 6.8" available from Chemtura Corporation, and "PLAS-CHECK 775" available from Ferro Corp. Other epoxidized vegetable oils for use in the invention include, for non-limiting example, epoxidized linseed oil sold under the trade designations "VIKOFLEX 7190" available from Arkema, Inc. and "DRAPEX 10.4" available from Chemtura Corporation, epoxidized cotton seed oil, epoxidized carthamus oil and mixtures thereof. Epoxidized soy bean oil is employed in some embodiments.

The hydroxyl functional (meth)acrylate may include without limitation 4-hydroxy butyl (meth)acrylate, hydroxyl ethyl (meth)acrylate, hydroxyl propyl (meth)acrylate and the like, as well as combinations thereof. Along with the hydroxyl functional (meth)acrylate, one or more hydroxyl functional materials may be present as diluents. Such hydroxyl functional materials may include without limitation alcohols, polyols, polyesters, polyethers, polycarbonates, and the like, as well as mixtures thereof. The hydroxyl functional (meth)acrylate and the hydroxyl functional material may each be present during the formation of the epoxy phosphate. The hydroxyl functional (meth)acrylate and the hydroxyl functional material may also each be present during the formation of the (meth)acrylate functional polyether polyol.

In some embodiments, the hydroxyl functional (meth)acrylate is present in an amount from about 1:99 to about 95:5 in a weight ratio of the hydroxyl functional (meth)acrylate to the epoxidized vegetable oil, and alternatively from about 5:95 to about 40:60. In some embodiments, the equivalent ratio of hydroxyl functionality of the hydroxyl functional (meth)acrylate to oxirane functionality in the epoxidized vegetable oil is from about 0.1:1 to about 3:1. In some embodiments, the equivalent ratio of hydroxyl functionality to oxirane functionality in the epoxidized vegetable oil is from about 0.2:1 to about 3:1. In some embodiments, the equivalent ratio of hydroxyl functionality to oxirane functionality in the epoxidized vegetable oil is about 0.2:1. The epoxidized vegetable oil may be present in an amount from about 1 to about 95 parts based on the total weight of the (meth)acrylate functional polyether polyol. The hydroxyl functional (meth)acrylate may be present in an amount of from about 1 to about 95 parts of the (meth)acrylate functional polyether polyol.

In certain embodiments, the (meth)acrylate functional polyether polyol may be present in an amount from about 1 to about 100 wt % of the coating composition.

The epoxy phosphate and the hydroxyl functional (meth)acrylate may be reacted in the presence of an acid catalyst. In some embodiments, the acid catalyst comprises a triflic acid, a triflate salt of a metal of Group IIA, IIB, IIIA, IIIB or VIIIA of the Periodic Table of Elements (according to the IUPAC 1970 convention), a mixture of the triflates salts, or a mixture thereof. The reaction may be at a temperature of about 50 to about 160° C. or from about 80 to about 120° C. In some embodiments, the acid catalyst has a dissociation constant in an aqueous solution (pKa) less than about 4. In some embodiments, the acid catalyst has a hydrophobe attached to the acid. In some embodiments, the amount of the acid catalyst can range from about 1 ppm to about 10,000 ppm, and alternatively from about 10 ppm to about 1,000 ppm, based on the total weight of the reaction mixture.

Acid catalysts additionally include, for non-limiting example, the Group IIA metal triflate catalysts such as without limitation magnesium triflate, the Group IIB metal triflate catalysts such as without limitation zinc and cadmium triflate, the Group IIIA metal triflate catalysts such as without limitation lanthanum triflate, the Group IIIB metal triflate catalysts such as without limitation aluminum triflate, and the Group VIIIA metal triflate catalysts such as without limitation cobalt triflate, and combinations thereof. Some embodiments of the invention employ an acid catalyst, such as a metal triflate catalyst, in the form of a solution in an organic solvent. Examples of solvents include, without limitation, water, alcohols such as n-butanol, ethanol, propanol, and the like, as well as aromatic hydrocarbon solvents, cycloaliphatic polar solvents such as, for non-limiting example, cycloaliphatic ketones (e.g. cyclohexanone), polar aliphatic solvents, such as, for non-limiting example, alkoxyalkanols, 2-methoxyethanol, non hydroxyl functional solvents, and mixtures thereof.

The reaction of the phosphoric acid compound with the epoxidized vegetable oil is rapid, even at low temperatures, so mixing the phosphoric acid compound into the hydroxyl functional (meth)acrylate helps to moderate this reaction and produce a more uniform epoxy phosphate. The epoxy phosphate may be formed by the addition of the phosphoric acid compound to the epoxidized vegetable oil at about 20 to about 100° C.

Radiation curable coating compositions of the invention can include conventional additives known to those skilled in the art, such as without limitation, flow agents, surface active agents, defoamers, anti-cratering additives, lubricants, and cure catalysts. In addition, (meth)acrylate monomers can be blended to control viscosity and di- and poly(meth)acrylate monomers and (meth)acrylate functional oligomers can be blended to achieve desired film properties.

In some embodiments of the invention, one or more coating compositions are applied to a substrate, such as for non-limiting example, cans, metal cans, easy-open-ends, packaging, containers, receptacles, can ends, or any portions thereof used to hold or touch any type of food or beverage. In some embodiments, one or more coatings are applied in addition to the coating compositions of the present invention, such as for non-limiting example, a prime coat may be applied between the substrate and the coating composition.

The coating compositions can be applied to substrates in any manner known to those skilled in the art. In some embodiments, the coating compositions are sprayed or roll coated onto a substrate. After the coating composition is applied, the coating composition may be cured with electron beam or ultraviolet radiation.

The resulting coating compositions are applied in some embodiments by conventional methods known in the coating industry. For substrates intended as beverage containers, the coating are applied in some embodiments at a rate in the range from about 0.5 milligrams to about 15 milligrams per square inch of polymer coating per square inch of exposed substrate surface. Radiation curable coating compositions are generally roll applied to flat substrates and then cured under UV lamps or electron beams. With electron beams, dosages of about 0.5 to 10 mrad are suitable for good cure under a nitrogen atmosphere.

EXAMPLES

The invention will be further described by reference to the following non-limiting examples. It should be understood that variations and modifications of these examples can be made by those skilled in the art without departing from the spirit and scope of the invention.

Example 1

Preparation of (Meth)Acrylate Functional Polyether Polyol 36 grams of butane diol monoacrylate and 0.5 grams of super phosphoric acid were added to 110 grams of epoxidized soy bean oil and 0.05 grams of phenothiazine with stirring at room temperature to form a mixture. The mixture was warmed to 90° C. in a water bath under an air purge. The mixture was stirred for 1 hour. Next, 36 grams of butane diol monoacrylate and 0.10 milliliters of Nacure Super A-218 (25% zinc triflate) were added to the mixture and held for 1 hour. A moderate exotherm was noted (to 98° C. in 20 minutes). Oxirane titration at the end of the reaction indicated that 99.9% conversion of the epoxide groups.

What is claimed is:

1. A radiation curable coating composition comprising a (meth)acrylate functional polyether polyol that is an acid catalyzed reaction product of an epoxy phosphate and a hydroxyl functional (meth)acrylate, wherein the epoxy phosphate is a reaction product of an epoxidized vegetable oil and a phosphoric acid compound.

2. The coating composition of claim 1, wherein the epoxy phosphate is formed in the presence of a hydroxyl functional material.

3. The coating composition of claim 1, wherein the hydroxyl functional (meth)acrylate is blended with a hydroxyl functional material.

4. The coating composition of claim 1, wherein the acid catalyst is at least one of a triflic acid, a triflate salt of a metal of Group IIA, IIB, IIIA, IIIB or VIIIA of the Periodic Table of Elements (according to the IUPAC 1970 convention), or a mixture of the triflate salts.

5. The coating composition of claim 1, wherein the hydroxyl functional (meth)acrylate is at least one of 4-hydroxy butyl (meth)acrylate, hydroxy ethyl (meth)acrylate, or hydroxyl propyl (meth)acrylate.

6. The coating composition of claim 1, wherein the phosphoric acid compound is at least one of phosphoric acid, super phosphoric acid, or an aqueous solution of the foregoing.

7. The coating composition of claim 1, wherein the phosphoric acid compound is present in an amount from about 0.001 to about 25 wt % of the (meth)acrylate functional polyether polyol.

8. A method of forming a (meth)acrylate functional polyether polyol, the method comprising:
   a) reacting an epoxidized vegetable oil with a phosphoric acid compound to form an epoxy phosphate; and
   b) reacting the epoxy phosphate with a hydroxyl functional (meth)acrylate in the presence of an acid catalyst to form a (meth)acrylate functional polyether polyol.

9. The method of claim 8, wherein the epoxy phosphate is formed in the presence of a hydroxyl functional material.

10. The method of claim 8, wherein the hydroxyl functional (meth)acrylate is blended with a hydroxyl functional material.

11. The method of claim 8, wherein the acid catalyst is at least one of a triflic acid, a triflate salt of a metal of Group IIA, IIB, IIIA, IIIB or VIIIA of the Periodic Table of Elements (according to the IUPAC 1970 convention), or a mixture of the triflates salts.

12. The method of claim 8, wherein the hydroxyl functional (meth)acrylate is at least one of 4-hydroxy butyl (meth)acrylate, hydroxy ethyl (meth)acrylate, or hydroxyl propyl (meth)acrylate.

13. The method of claim 8, wherein the phosphoric acid compound is at least one of phosphoric acid, super phosphoric acid, or an aqueous solution of the foregoing.

14. The method of claim 8, wherein the phosphoric acid compound is present in an amount from about 0.01 to about 25 wt % of the (meth)acrylate functional polyether polyol.

15. A substrate coated with the coating composition of claim 1.

16. A radiation curable coating composition including the (meth)acrylate functional polyether polyol of claim 8.

17. A method of coating a substrate comprising the steps of:
   a) applying the coating composition of claim 1 to the substrate; and
   b) curing the coating composition with electron beam or ultraviolet radiation.

18. A substrate coated with the coating composition of claim 1.

* * * * *